United States Patent
Li et al.

(10) Patent No.: US 12,128,049 B2
(45) Date of Patent: *Oct. 29, 2024

(54) DOSAGE REGIMEN OF PALIPERIDONE PALMITATE EXTENDED-RELEASE INJECTABLE SUSPENSION

(71) Applicant: Luye Innomind Pharma Shijiazhuang Co., Ltd., Shijiazhuang (CN)

(72) Inventors: Youxin Li, Shandong (CN); Chunjie Sha, Shandong (CN); Fengjuan Zhao, Shandong (CN); Changbing Tu, Shandong (CN); Kaoxiang Sun, Shandong (CN); Wanhui Liu, Shandong (CN); Lifang Sun, Shandong (CN); Ying Meng, Shandong (CN)

(73) Assignee: Luye Innomind Pharma Shijiazhuang Co., Ltd., Shijiazhuang (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/305,303

(22) Filed: Apr. 21, 2023

(65) Prior Publication Data
US 2023/0248732 A1   Aug. 10, 2023

Related U.S. Application Data

(63) Continuation of application No. 16/759,287, filed as application No. PCT/US2018/057858 on Oct. 26, 2018, now Pat. No. 11,666,573.

(60) Provisional application No. 62/647,333, filed on Mar. 23, 2018, provisional application No. 62/578,082, filed on Oct. 27, 2017.

(51) Int. Cl.
*A61K 31/519* (2006.01)
*A61K 9/00* (2006.01)

(52) U.S. Cl.
CPC .......... *A61K 31/519* (2013.01); *A61K 9/0019* (2013.01)

(58) Field of Classification Search
CPC ..................... A61K 31/519; A61K 9/0019
See application file for complete search history.

(56) References Cited

U.S. PATENT DOCUMENTS

| | | | |
|---|---|---|---|
| 6,555,544 B2 | 4/2003 | François et al. |
| 9,320,707 B2 | 4/2016 | François et al. |
| 9,439,906 B2 | 9/2016 | Vermeulen et al. |
| 2009/0163519 A1 | 6/2009 | Vermeulen et al. |
| 2017/0281629 A1 | 10/2017 | Gopal et al. |

FOREIGN PATENT DOCUMENTS

| | | |
|---|---|---|
| CA | 2 655 335 A1 | 6/2009 |
| WO | 2016/199170 A2 | 12/2016 |

OTHER PUBLICATIONS

Invega Sustenna, Dosing & Administration-Once monthly Invega Sustenna, Mar. 2017 (Year: 2017).*
"Dosing & Administration—Once Monthly Invega Sustenna," retrieved Jan. 28, 2019, from URL=https://www.invegasustennahcp.com/sites/www.invegasustennahcp-vl.com/files/Invega_Sustenna_Dosing_And_Administration_Guide.pdf?v=16, Mar. 2017. (12 pages).
"Invega Sustennar paliperidone palmitate New Zealand Datasheet," retrieved Jan. 29, 2019, from URL=http://www.janssen.com/newzealand/sites/www_janssen_com_newzealand/files/prod_files/live/invegasustennainj.pdf, May 2017. (31 pages).
Chue et al., "A review of paliperidone palmitate," *Expert Review of Neurotherapeutics* 12(12):1383-1397, 2012. (Abstract Only).
Greenberg et al., "Paliperidone Palmitate for Schizoaffective Disorder: A Review of the Clinical Evidence," *Neruol Ther* 4:81-91, 2015. (Published Online: Jul. 23, 2015).
International Search Report and Written Opinion, mailed Feb. 11, 2019, of International Application No. PCT/US2018/057858, 16 pages.

\* cited by examiner

*Primary Examiner* — Jean P Cornet
(74) *Attorney, Agent, or Firm* — Seed IP Law Group LLP

(57) ABSTRACT

Provided herein are simplified dosing regimens for administering paliperidone palmitate to a patient in need of treatment of schizophrenia or schizoaffective disorders.

23 Claims, 9 Drawing Sheets

DOSAGE REGIMEN OF PALIPERIDONE PALMITATE EXTENDED-RELEASE INJECTABLE SUSPENSION

CROSS-REFERENCE TO RELATED APPLICATION

This application is a continuation application of U.S. patent application Ser. No. 16/759,287, filed Apr. 24, 2020, which is a U.S. National Stage Patent Application of International Application No. PCT/US2018/057858, filed Oct. 26, 2018, which claims the benefit of U.S. Provisional Patent Application No. 62/578,082, filed Oct. 27, 2017, and U.S. Provisional Patent Application No. 62/647,333, filed Mar. 23, 2018, which applications are incorporated herein in their entireties.

BACKGROUND

Technical Field

This disclosure relates to methods of treating psychosis or other psychiatric disorders with extended release paliperidone palmitate injectable suspension.

Description of the Related Art

Paliperidone palmitate is used for the treatment of schizophrenia alone or used in schizoaffective disorders as an adjunctive therapy to antidepressants. It is presently available in an extended release oral tablet (INVEGA® by Jansen Pharmaceuticals) or long acting extended release aqueous injectable suspension suitable for intramuscular (IM) administration (INVEGA SUSTENNA® by Jansen Pharmaceuticals). The intramuscular product has been approved and marketed in the U.S. since 2006.

Paliperidone palmitate undergoes hydrolysis to yield paliperidone, the major active metabolite of risperidone. The injectable formulation is for intramuscular use and has been clinically demonstrated to be safe, well tolerated and with a high efficacy. Its prolonged release and duration of action are attributed to its slow dissolution rate and subsequent hydrolysis to paliperidone.

Given its unique dissolution profile, current paliperidone palmitate therapy requires that two initial loading doses be given one week apart, followed by regular monthly maintenance doses. See, e.g., U.S. Pat. No. 9,439,906. In particular, INVEGA SUSTENNA® has five strengths at, in descending order, 234 mg, 156 mg, 117 mg, 78 mg and 39 mg of paliperidone palmitate, which are equivalents of 150 mg, 100 mg, 75 mg, 50 mg and 25 mg of paliperidone, respectively. According to its label, INVEGA SUSTENNA® is intended to be administered at its highest strength of 234 mg (i.e., 150 mg paliperidone) on day 1 followed by a second loading dose of 156 mg (i.e., 100 mg paliperidone) on day 8. Thereafter, a monthly maintenance dose of 117 mg (i.e., 75 mg paliperidone) is recommended. It is believed that after the initial two loading doses, serum concentration of the active metabolite can rapidly reach therapeutic level and approach the steady-state concentration, which can be further maintained by subsequent monthly maintenance doses. The maintenance dosages may vary from 39 to 234 mg (i.e., 25 mg-150 mg paliperidone) per month depending on tolerability and efficacy with respect to the individual patient. The standard INVEGA SUSTENNA® regimens are referred to herein as "RLD regimens."

Paliperidone palmitate therapy such as INVEGA SUSTENNA® requires two loading doses one week apart in order to rapidly attain therapeutic plasma concentrations. Despite being long-acting in the maintenance period, current therapy compels patient compliance at the initial dosing stage when the patient is the least capable. There exists a need in the art for improved dosage regimen in administering long-acting paliperidone palmitate injectable suspension.

BRIEF SUMMARY

Figure 1:
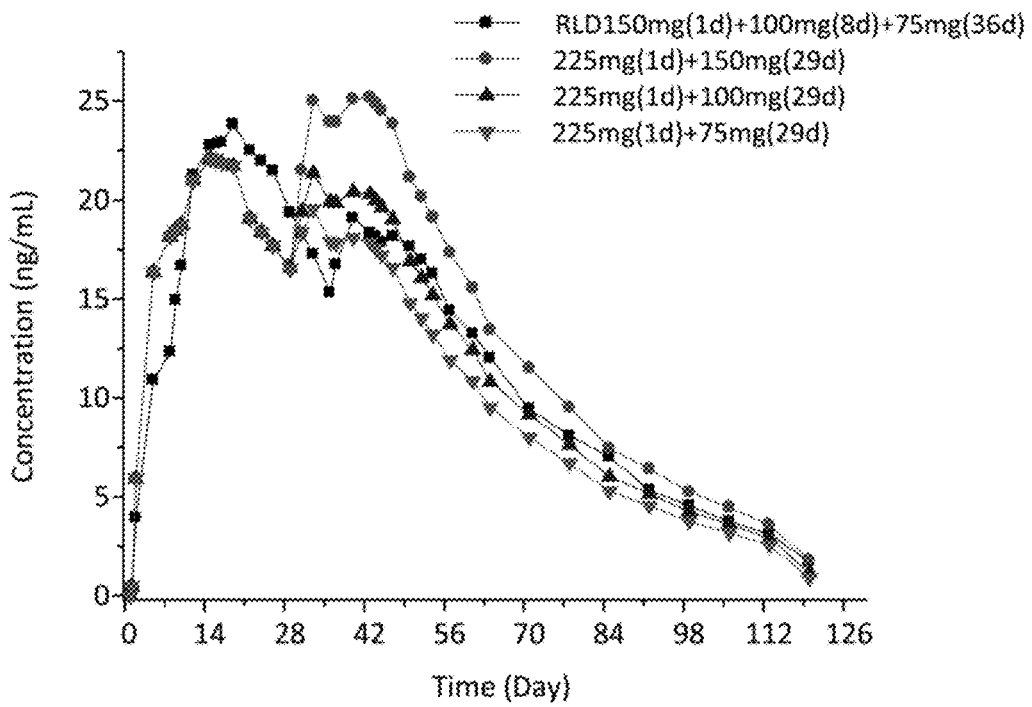
FIG. 1 shows the preliminary pharmacokinetic (PK) modeling and simulation of a single, heightened loading dose followed by a maintenance dose according to an embodiment.

Various embodiments provide dosing regimens having alternative initial loading doses, which dosing regimens address the drawbacks of the currently available therapy such as INVEGA SUSTENNA® while achieving a comparable level of systemic exposure during and following the initial dosing phrase. The represent disclosure demonstrates by pharmacokinetic results that it is feasible to achieve comparable systemic exposure by alternative dosing regimens. As such, some of the initial dosing regimens may be able to improve the patient convenience and, hence, increase compliance.

One embodiment provides a dosing regimen having a single, heightened initial loading dose followed by monthly maintenance doses. This simplified dosing regimen obviates two loading doses at the initial dosing stage, thereby enhancing patient compliance without compromising therapeutic effect. More specifically, it is provided a dosing regimen for administering paliperidone palmitate to a patient in need of treatment of schizophrenia or schizoaffective disorders, the dosing regimen comprising:

(1) administering intramuscularly to the patient a first loading dose of 200 mg-300 mg of paliperidone as paliperidone palmitate on the first day of treatment;

(2) beginning on the 29th day±7 days from the first loading dose, administering intramuscularly to the patient monthly maintenance dose in the range of 25 mg-150 mg of paliperidone as paliperidone palmitate, wherein paliperidone palmitate is formulated in an aqueous suspension formulation.

In more specific embodiments, the first loading dose comprises 225 mg of paliperidone as paliperidone palmitate.

In preferred embodiment, the first monthly maintenance dose is in the range of 50 mg-150 mg, or more preferably, 100 mg of paliperidone as paliperidone palmitate. Thereafter, the maintenance doses may be in the range of 25 mg-150 mg paliperidone as paliperidone palmitate, depending on tolerability and efficacy of the therapy for individual patient.

A further embodiment provides yet another dosing regimen for administering paliperidone palmitate to a patient in need of treatment of schizophrenia or schizoaffective disorders, the dosing regimen comprising:

(1) administering intramuscularly to the patient a first loading dose of 150 mg-225 mg of paliperidone as paliperidone palmitate on the first day of treatment;

(2) administering intramuscularly to the patient a second loading dose of 50 mg-100 mg of paliperidone as paliperidone palmitate on the 15th day±3 days from the first day of treatment;

(3) beginning on the 36th day±7 days from the first loading dose, administering intramuscularly to the patient monthly maintenance dose of 25 mg-150 mg of paliperidone as paliperidone palmitate, wherein paliperidone palmitate is formulated in an aqueous suspension formulation.

In more specific embodiments, the first loading dose comprises 200 mg of paliperidone as paliperidone palmitate.

In a preferred embodiment, the second loading dose is 50 mg of paliperidone as paliperidone palmitate. In other embodiments, the first monthly maintenance does is 75 mg. Thereafter, the maintenance doses may be in the range of 25 mg-150 mg (e.g., 75 mg) paliperidone as paliperidone palmitate, depending on tolerability and efficacy of individual patient.

DETAILED DESCRIPTION

Paliperidone Palmitate Injectable Suspension

The active ingredient of the intramuscular (IM) injectable suspension is paliperidone palmitate. Paliperidone palmitate is the palmitate ester of paliperidone, the major active metabolite of risperidone. The chemical name is (9RS)-3-[2-[4-(6-Fluoro-1,2-benzisoxazol-3-yl) piperidin-1-yl] ethyl]-2-methyl-4-oxo-6,7,8,9-tetrahydro-4H-pyrido[1,2-a]pyrimadin-9-yl hexadecanoate. The manufacturing process of paliperidone palmitate comprises a single synthetic step of esterification of paliperidone with palmitic acid, followed by a sterilization process.

Paliperidone palmitate is practically insoluble in aqueous media over a broad pH range. This low solubility allows the drug substance to be formulated as an aqueous suspension for IM injection, which provides an extended release profile that is a function of drug substance particle size.

Paliperidone palmitate can be micronized to desired sizes, which are generally less than 100 microns, or more typically less than 10 microns, including submicron ranges (i.e., nanometer ranges). The particle sizes can impact the dissolution of paliperidone palmitate, which in turn can impact the release rate of the active metabolite. Typically, larger particles are slower to dissolve and therefore slower to release the active metabolite. Micronization of paliperidone palmitate can be carried out by methods known in the art, including those disclosed in U.S. Pat. No. 9,439,906.

The paliperidone palmitate particle sizes can be characterized by size distribution within a sample. In certain embodiments, 90% of the particles are less than 100 µm in diameters (e.g., d(0.9) is 100 µm). In other embodiments, 90% of the particles are less than 10 µm (e.g., d(0.9) is 10 µm). In other embodiments, 90% of the particles are less than 5 µm (e.g., d(0.9) is 5 µm). In certain embodiments, the mass median diameter (d(0.5)), i.e., the size where 50% of the particles are above and 50% of the particles are below, is in the range of 100 nm-2 µm. In further embodiments, the mass median diameter is in the range of 500 nm-1.6 µm. In further embodiments, the mass median diameter is about 900 nm-1.2 µm.

Particle sizes of paliperidone palmitate may also be characterized by specific surface area (SSA). As used herein, the particle sizes of paliperidone palmitate may be in the range of 2-15 $m^2/g$. In certain embodiments, the particle sizes are in the range of 5-11 $m^2/g$. In other embodiments, the particle sizes are in the range of 2-8 $m^2/g$, or in the range of 7-10 $m^2/g$, or in the range of 10-12 $m^2/g$, or in the range of 10-15 $m^2/g$.

Paliperidone palmitate can be formulated as a suspension in any pharmaceutically acceptable diluent including, for example, water. The suspension may further include one or more additives such as buffer, isotonizing agent, preservatives, surfactants, wetting agents suspending agents, and the like.

Suitable suspending agents for use in the aqueous suspensions according to the present invention are cellulose derivatives, e.g. methyl cellulose, sodium carboxymethyl cellulose and hydroxypropyl methyl cellulose, polyvinylpyrrolidone, alginates, chitosan, dextrans, gelatin, polyethylene glycols, polyoxyethylene- and polyoxypropylene ethers. Preferably sodium carboxymethyl cellulose is used in a concentration of 0.5 to 2%, most preferably 1% (w/v).

Suitable wetting agents for use in the aqueous suspensions according to the present invention are polyoxyethylene derivatives of sorbitan esters, e.g. polysorbate 20 and polysorbate 80, lecithin, polyoxyethylene- and polyoxypropylene ethers, sodium deoxycholate. Preferably polysorbate 20 is used in a concentration of 0.5 to 3%, more preferably 0.5 to 2%, most preferably 1.1% (w/v).

Suitable buffering agents are salt of weak acids and should be used in amount sufficient to render the dispersion neutral to very slightly basic (pH is 7.0-8.5), preferably in the pH range of 7 to 7.5. Particularly preferred is the use of a mixture of disodium hydrogen phosphate (anhydrous) (typically about 0.9% (w/v)) and sodium dihydrogen phosphate monohydrate (typically about 0.6% (w/v)). This buffer also renders the dispersion isotonic and, in addition, less prone to flocculation of the ester suspended therein.

Preservatives are antimicrobials and anti-oxidants which can be selected from the group consisting of benzoic acid, benzyl alcohol, butylated hydroxyanisole, butylated hydroxytoluene, chlorbutol, a gallate, a hydroxybenzoate, EDTA, phenol, chlorocresol, metacresol, benzethonium chloride, myristyl-gamma-piccolinium chloride, phenylmercuric acetate and thimerosal. In particular, it is benzyl alcohol which can be used in a concentration up to 2% (w/v), preferably up to 1.5% (w/v).

Isotonizing agents are, for example, sodium chloride, dextrose, mannitol, sorbitol, lactose, sodium sulfate. The suspensions conveniently comprise from 0 to 10% (w/v) isotonizing agent. Mannitol may be used in a concentration from 0 to 7% More preferably, however, from about 1 to about 3% (w/v), especially from about 1.5 to about 2% (w/v) of one or more electrolytes are used to render the suspension isotonic, apparently because ions help to prevent flocculation of the suspended ester. In particular, electrolytes of the buffer serve as isotonizing agent.

Additional detailed description of the preparation of paliperidone palmitate suspension may be found in U.S. Pat. Nos. 6,555,544, 9,439,906, which are incorporated herein by reference in their entireties.

In various embodiments, the aqueous suspension formulations may comprise, by the weight percentage based on the total weight of the formulation: (a) from 3 to 20% (w/w) of paliperidone palmitate; (b) from 0.5 to 2% (w/w) of a wetting agent; (c) one or more buffering agents sufficient to render the composition neutral to very slightly basic (pH 8.5); (d) from 0.5 to 4% (w/w) of a suspending agent; (e) up to 2% (w/w) preservatives; and (f) water q.s. ad 100%. Preferably the aqueous suspension will be made under sterile conditions and no preservatives will be used.

In preferred embodiments, the aqueous suspension formulation is an aqueous suspension of particulate paliperidone palmitate having the size distribution as disclosed herein. Suitable additives include polysorbate 20, polyethylene glycol 4000, citric acid monohydrate, disodium hydrogen phosphate anhydrous, sodium dihydrogen phosphate monohydrate, sodium hydroxide. The amount of paliperidone palmitate in the aqueous suspension formulation may be: 39 mg, 78 mg, 117 mg, 156 mg, 234 mg, 312 mg, 351 mg, 390 mg and 468 mg, which correspond to 25 mg, 50 mg, 75 mg, 100 mg, 150 mg, 200 mg, 225 mg, 250 mg and 300 mg of paliperidone, respectively. In various embodiments, the concentration of paliperidone palmitate in aqueous suspension formulation is about 15 w/w %.

Dosage Regimen

Based on the collective comparable in vitro dissolution data, the preclinical animal PK data and the preliminary pharmacokinetic (PK) modeling and simulation using available human PK data of INVEGA SUSTENNA®, provided herein are alternative dosing regimens having simplified initial dosing phases while achieving a superior or comparable level of systemic exposure of paliperidone to that of the initial dosing regimen of INVEGA SUSTENNA®. Advantageously, the dosing regimens are capable of enhancing patient compliance, especially during the initial dosing phase when patient compliance is critical in achieving adequate efficacy that may induce future compliance during the maintenance period.

Thus, one embodiment provides a dosing regimen having a single, heightened initial loading dose followed by monthly maintenance doses. This simplified dosing regimen obviates two loading doses at the initial dosing stage, thereby enhancing patient compliance without compromising therapeutic effect. More specifically, provided is a dosing regimen for administering paliperidone palmitate to a patient in need of treatment of schizophrenia or schizoaffective disorders, the dosing regimen comprising:

(1) administering intramuscularly to the patient a first loading dose of 200 mg-300 mg of paliperidone as paliperidone palmitate on the first day of treatment;

(2) beginning on the 29th day±7 days from the first loading dose, administering intramuscularly to the patient monthly maintenance dose in the range of 25 mg-150 mg—of paliperidone as paliperidone palmitate, wherein paliperidone palmitate is formulated in an aqueous suspension formulation.

In a preferred embodiment, the first loading dose comprises 225 mg of paliperidone as paliperidone palmitate.

As used herein, a "loading dose" is a heightened dose typically given at the beginning of a course of treatment. The first loading dose is given on the first day (day 1) of the treatment and is at a higher amount than any of the doses given thereafter. Loading dose is typically followed by maintenance doses given at regular intervals, although sometimes a second loading dose may be given after the first loading dose and before the maintenance doses.

As used herein, "monthly maintenance dose" refers to regularly administered injection within about four weeks (28 days±7 days) from the immediate preceding dose. The immediate preceding dose may be the initial loading dose. Thus, according to this embodiment, the first monthly maintenance dose begins on the 29th day (or within a window of ±7 days thereof) from the initial loading dose on day 1. The second monthly maintenance dose begins on the 29th day (within a window of ±7 days thereof) from the immediate preceding dose (e.g., the first monthly maintenance dose), and so forth.

During the maintenance period in which regular monthly injections are given, each dosing strength may be the same or different. In a preferred embodiment, the first monthly maintenance dose is in the range of 50-150 mg paliperidone as paliperidone palmitate, or more specifically, 100 mg of paliperidone as paliperidone palmitate. Thereafter, the one or more further monthly maintenance doses may be in the range of 25 mg-150 mg paliperidone as paliperidone palmitate, depending on tolerability and efficacy of the therapy on individual patient. Specifically, the monthly maintenance doses may be 150 mg, 100 mg, 75 mg, 50 mg, or 25 mg of paliperidone as paliperidone palmitate. In a preferred embodiment, the further monthly maintenance doses are 75 mg of paliperidone as paliperidone palmitate.

FIG. 1 shows the preliminary pharmacokinetic modeling and simulation. As shown, a single, heightened loading dose of 225 mg is followed by a maintenance dose in different strengths within 28 days (i.e., given on the 29th day from the loading dose administered on the first day). The PK profiles closely track the PK profile of INVEGA SUSTENNA® dosing regimen according to its label (i.e., the "RLD" regimen), indicating that a sufficiently high therapeutic level of the active substance is achieved under the simplified regimen having a single loading dose.

A further embodiment provides yet another dosing regimen by which two initial loading doses are administered about two weeks (14 days) apart, followed by monthly maintenance doses. More specifically, it is provided a dosing regimen for administering paliperidone palmitate to a patient in need of treatment of schizophrenia or schizoaffective disorders, the dosing regimen comprising:

(1) administering intramuscularly to the patient a first loading dose of 150 mg-225 mg of paliperidone as paliperidone palmitate on the first day of treatment;

(2) administering intramuscularly to the patient a second loading dose in the range of 50-100 mg of paliperidone as paliperidone palmitate on the 15th day±3 days from the first day of treatment;

(3) beginning on the 36th day±7 days from the first loading dose, administering intramuscularly to the patient monthly maintenance dose of 25 mg-150 mg of paliperidone as paliperidone palmitate formulated in an aqueous suspension formulation.

In preferred embodiments, the second loading dose is 50 mg paliperidone as paliperidone palmitate. In other embodiments, the first monthly maintenance dose is 75 mg of paliperidone as paliperidone palmitate. Thereafter, the one or more further monthly maintenance doses may be in the range of 25 mg-150 mg paliperidone as paliperidone palmitate, depending on tolerability and efficacy of the therapy on the individual patient. Specifically, the monthly maintenance doses may be 150 mg, 100 mg, 75 mg, 50 mg, or 25 mg of paliperidone as paliperidone palmitate.

Figure 2:
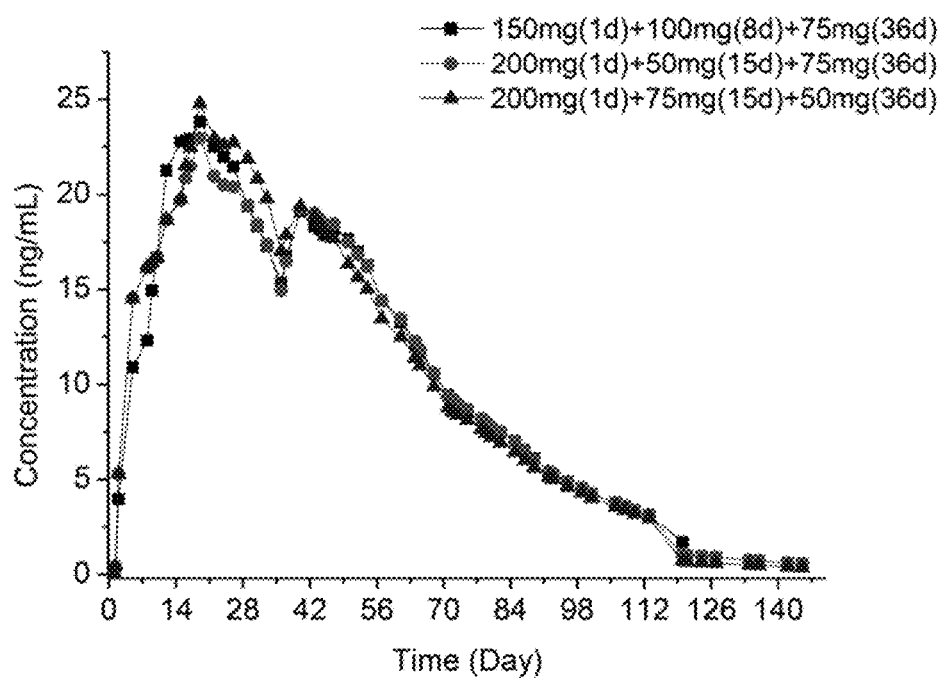
FIG. 2 demonstrates that the PK profiles according an embodiment of the present disclose as compared to the dosage regimen (RLD regimen) according to the label for INVEGA SUSTENNA®.

FIG. 2 demonstrates that, in simulation, the PK profiles according to the above embodiment track closely to that of INVEGA SUSTENNA® (shown as having an initial loading dose of 150 mg on day 1).

Figure 3:
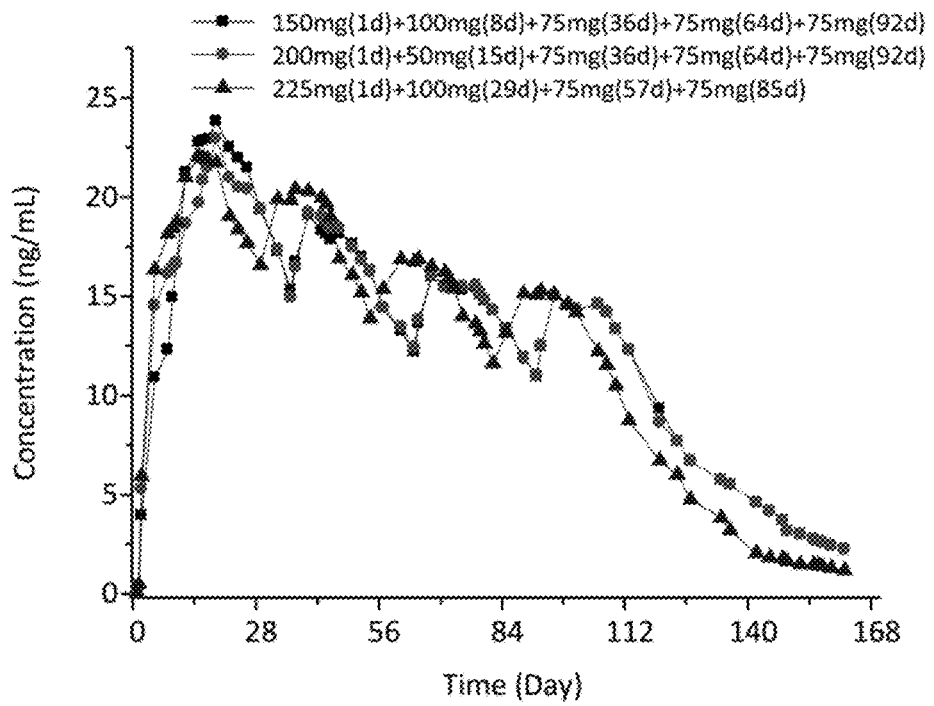
FIG. 3 demonstrates that the PK profiles of longer treatment into the maintenance period according to the dosing regimens disclosed herein and as compared to INVEGA SUSTENNA® regimen.

FIG. 3 demonstrates that, in simulation, the PK profiles of longer treatment into the maintenance period according to the dosing regimens disclosed herein also track closely to the conventional therapy, further indicating the efficacy of the improved dosing regimens.

Treatment of Psychosis or Psychiatric Disorders

The therapy disclosed herein is suitable for treating or alleviating the symptoms of psychosis and psychiatric disorders in patients for all the known uses of risperidone. These mental disorders include, but are not limited to, schizophrenia; bipolar disorder or other disease states in which psychosis, aggressive behavior, anxiety or depression is evidenced. Schizophrenia refers to conditions characterized as schizophrenia, schizoaffective disorder and schizophreniform disorders, in DSM-IV-TR such as category 295.xx.

EXAMPLES

Example 1

Drug Product

The injectable paliperidone palmitate describe herein is developed as a white to off-white sterile aqueous extended-release suspension for intramuscular injection. Table 1 shows paliperidone palmitate injectable suspension in various strengths. In addition to the active paliperidone palmitate, other components are listed by their respective weight and w/w percentages. Other strengths, including 312 mg, 351 mg, 390 mg and 468 mg of paliperidone palmitate, can be prepared by proportionally adjusting the various ingredients in the formulations.

TABLE 1

| Compositions | Unit Formula (mg) | | | | | Percentage (w/w %) |
|---|---|---|---|---|---|---|
| | 39 mg | 78 mg | 117 mg | 156 mg | 234 mg | |
| Paliperidone palmitate | 39 | 78 | 117 | 156 | 234 | 15.04 |
| Citric acid monohydrate | 1.25 | 2.50 | 3.75 | 5.00 | 7.50 | 0.48 |
| Disodium hydrogen phosphate anhydrous | 1.25 | 2.50 | 3.75 | 5.00 | 7.50 | 0.48 |
| Sodium dihydrogen phosphate monohydrate | 0.62 | 1.25 | 1.88 | 2.50 | 3.75 | 0.24 |
| Sodium hydroxide | 0.71 | 1.42 | 2.13 | 2.84 | 4.27 | 0.27 |
| Polyethylene glycol 4000 | 7.5 | 15.0 | 22.5 | 30.0 | 45.0 | 2.89 |

TABLE 1-continued

| Compositions | Unit Formula (mg) | | | | | Percentage (w/w %) |
|---|---|---|---|---|---|---|
| | 39 mg | 78 mg | 117 mg | 156 mg | 234 mg | |
| Polysorbate 20 | 3 | 6 | 9 | 12 | 18 | 1.16 |
| Water for Injection | 206 | 412 | 618 | 824 | 1236 | 79.43 |

Paliperidone palmitate is micronized aseptically using wet milling. The aseptic wet milling process uses a type of milling beads in the mill machine to obtain particles of micronized paliperidone palmitate with desired size distribution. In this process, the sterility of the final product is ensured by using a sterilization filtration and aseptic process. The injectable suspension is provided in a prefilled syringe with a plunger stopper and tip cap. The kit also contains 2 safety needles (a 1½-inch 22 gauge safety needle and a 1-inch 23 gauge safety needle). Table 2 shows that the particle size distributions in the paliperidone palmitate injectable suspension are the same or comparable to those of the commercial INVEGA SUSTENNA®.

TABLE 2

| Samples | Size distribution (μm) | | |
|---|---|---|---|
| | d(0.1) | d(0.5) | d(0.9) |
| Example 1 | 0.449 | 0.995 | 2.504 |
| INVEGA SUSTENNA ® | 0.497 | 1.067 | 2.598 |

Figure 4:
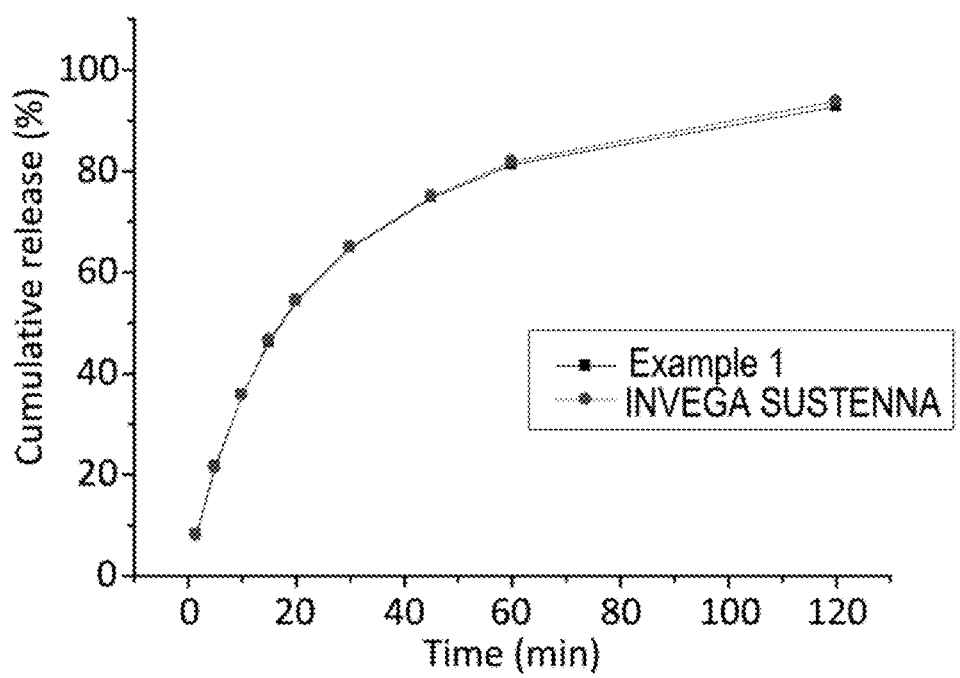
FIG. 4 shows the in vitro release profile of the drug product described in Example 1 as compared to that of INVEGA SUSTENNA®.

The in vitro release of the injectable suspension is evaluated by the FDA recommended dissolution method for paliperidone palmitate extended release suspension using USP Type II (paddle) apparatus with 900 mL 0.001 M HCl containing 0.489% Polysorbate 20 at temperature 25±0.5° C. at 50 rpm. The results showed that the in vitro release profile of Example 1 is identical to that of INVEGA SUSTENNA® (FIG. 4).

The paliperidone palmitate injectable suspension includes the following strengths: 39 mg, 78 mg, 117 mg, 156 mg, 234 mg, 312 mg, 351 mg, 390 mg and 468 mg which correspond to 25 mg, 50 mg, 75 mg, 100 mg, 150 mg, 200 mg, 225 mg, 250 mg and 300 mg of paliperidone, respectively.

Example 2

In Vivo Animal Study Based on a Single Dose

A pharmacokinetic study in Beagle dogs indicated that following intramuscular administration, the plasma exposure of 3.1 mg/kg of the injectable suspension of Example 1 (based on the paliperidone palmitate) was comparable to that of 3.1 mg/kg of INVEGA SUSTENNA®. In support of the rationale for the proposed development program, preclinical studies in beagle dogs were performed. Beagle dogs were randomly divided in two groups (five animals/group/sex). Group 1 received single IM injection of Example 1 at 3.1 mg/kg, and Group 2 received single IM injection of INVEGA SUSTENNA® at 3.1 mg/kg. Blood samples (1.0 mL) was collected at pre-dose and 1 h, 6 h, 1 d, 2 d, 4 d, 7 d, 9 d, 11 d, 14 d, 17 d, 21 d, 24 d, 28 d, 31 d, 35 d post dose. Paliperidone was determined by LC-MS/MS method.

Figure 5:
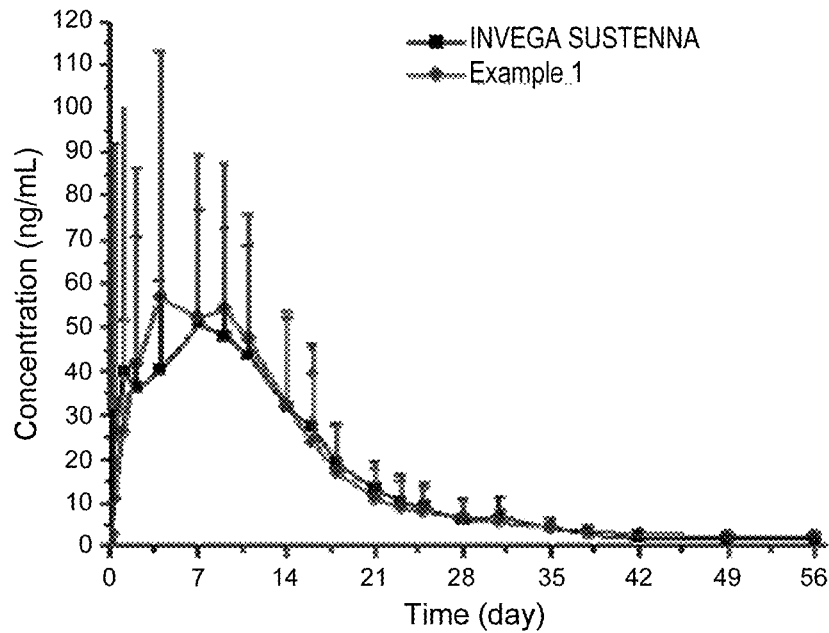
FIG. 5 shows the respective mean plasma concentration-time profiles of paliperidone after a single IM injection of Example 1 and INVEGA SUSTENNA®.

The mean plasma concentration-time profiles of paliperidone after a single IM injection of Example 1 and INVEGA SUSTENNA® were shown in FIG. 5. Summary pharmacokinetic parameters are presented in Table 3.

TABLE 3

Pharmacokinetic parameters of paliperidone after a single IM injection of Example 1 and INVEGA SUSTENNA® in dogs (n = 10)

| | Parameters | | | | |
|---|---|---|---|---|---|
| | $T_{max}$ | $C_{max}$ | F-$C_{max}$ Unit | $AUC_{(0-t)}$ | F-$AUC_{(0-t)}$ |
| | Day | µg/L | % | µg/L*d | % |
| Example 1 | 8.20 ± 3.55 | 73.01 ± 53.84 | 101.91 | 896.27 ± 460.43 | 104.80 |
| INVEGA SUSTENNA® | 8.73 ± 4.78 | 71.64 ± 56.92 | — | 855.23 ± 382.01 | — |

The relative bioavailability (AUC) of Example 1 in dogs was 104.80% and $C_{max}$ was 101.91%, respectively, when compared to INVEGA SUSTENNA® at an equivalent i.m. dose of 3.1 mg/kg.

Example 3

Monthly Dosing Having High Initial Loading Dose—a Simulated Study

Figure 6:
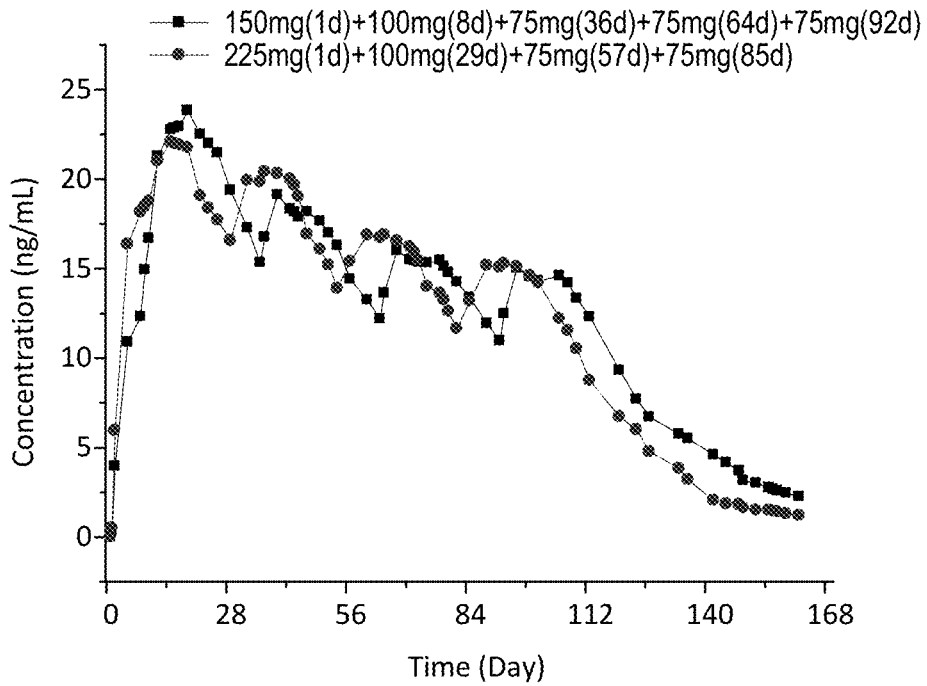
FIG. 6 demonstrates the PK profiles of the simplified dosing regimen having a heightened initial loading dose followed by monthly maintenance doses according to an embodiment.

The simplified dosing regimen according on one embodiment comprises a high loading dose followed by monthly maintenance doses for the drug product of Example 1. The regimen requires one fewer dose initially and allows for a longer interval between the first loading dose and the subsequent maintenance dose, when compared to the standard INVEGA SUSTENNA® dosing regimen (RLD regimen). FIG. 6 demonstrates the simulated PK profiles of the simplified dosing regimen disclosed herein having a heightened initial loading dose following by monthly maintenance doses compared to the simulated PK profile of the RLD regimen.

The clinical simulations show a faster onset of drug release and less fluctuations in the plasma profiles over the first two months and comparability thereafter. The following table summarizes the analysis including partial AUC breakdowns.

TABLE 4

| Parameters | RLD Regimen 150 mg(1 d) + 100 mg(8 d) + 75 mg(36 d) + 75 mg(64 d) + 75 mg(92 d) | Simplified Dosing Regimen with high initial loading dose 225 mg(1 d) + 100 mg(29 d) + 75 mg(57 d) + 75 mg(85 d) |
|---|---|---|
| Total Dose (mg) | 475 | 475 |
| $T_{max}$ (day) | 19 | 15 |
| $C_{max}$ (ng/mL) | 23.83 | 22.05 |

TABLE 4-continued

| Parameters | RLD Regimen 150 mg(1 d) + 100 mg(8 d) + 75 mg(36 d) + 75 mg(64 d) + 75 mg(92 d) | Simplified Dosing Regimen with high initial loading dose 225 mg(1 d) + 100 mg(29 d) + 75 mg(57 d) + 75 mg(85 d) |
|---|---|---|
| $AUC_{1-15\,d}$(d*ng/mL) | 192.04 | 228.64 |
| F-AUC(%) | — | 119.06 |
| $AUC_{1-31\,d}$(d*ng/mL) | 540.89 | 537.86 |
| F-AUC(%) | — | 99.44 |
| $AUC_{1-61\,d}$(d*ng/mL) | 1046.53 | 1085.38 |
| F-AUC(%) | — | 103.71 |
| $AUC_{last}$(d*ng/mL) | 2106.73 | 2098.17 |
| F-AUC(%) | — | 99.59 |
| F-$C_{max}$(%) | — | 92.52 |

Example 4

Pharmacokinetic Studies of Dosing Regimens in Animal Testing

Animal testing was also carried out to analyze the in vivo PK behaviors under the various dosing regimens disclosed herein.

Test Animals 20 healthy male beagle dogs (average weight about 11 kg) were randomly divided into 5 groups (Groups I-V) with 4 dogs in each group. Each animal was assigned its own number (#1-#20).

Dosing Regimens

Group I animals (#1-#4) and Group IV animals (#13-#16) were tested under RLD regimen. Group II animals (#5-#8) were tested under Regimen A. Group III animals (#9-#12) and Group V animals (#17-#20) were tested under Regimen B. Table 5 summarizes the respective human dosages (mg of paliperidone) and the equivalent animal dosages (converted to mg/kg) and the dosing intervals under each dosing regimen.

TABLE 5

| Dosing Regimens | | Day 1 | Day 8 | Day 15 | Day 29 | Day 36 |
|---|---|---|---|---|---|---|
| RLD | Human | 150 mg | 100 mg | | | 75 mg |
| | Group I | 4.6 mg/kg | 3.1 mg/kg | | | 2.3 mg/kg |
| | Group IV | 4.6 mg/kg | 3.1 mg/kg | | | 2.3 mg/kg |
| Regimen A | Human | 200 mg | | 50 mg | | 75 mg |
| | Group II | 6.2 mg/kg | | 1.5 mg/kg | | 2.3 mg/kg |

TABLE 5-continued

| Dosing Regimens | | Day 1 | Day 8 | Day 15 | Day 29 | Day 36 |
|---|---|---|---|---|---|---|
| Regimen B | Human | 225 mg | | | 100 mg | |
| | Group III | 6.9 mg/kg | | | 3.1 mg/kg | |
| | Group V | 6.9 mg/kg | | | 3.1 mg/kg | |

Sample Collection

The animals in each group received intramuscular injections according to the dosing regimen assigned to the group. Blood samples (1 ml/collection) were collected from the forelimb vein of each beagle immediate before administration (at 0 h), and thereafter at time intervals of 6 h (day 1), 24 hr (day 2), day 3, day 5, day 8 (prior to dosing for groups receiving RLD regimen), day 9, day 11, day 13, day 15 (prior to dosing for groups receiving Regimen A), day 17, day 19, day 22, day 24, day 26, day 29 (prior to dosing for groups receiving Regimen A), day 30, day 32, day 34, day 36 (prior to dosing for groups receiving RLD and Regimen A), day 37, day 39, day 42, day 45, day 47, day 50, day 53, day 57, day 64, day 71, day 78, and day 85. The blood samples were placed in heparinized centrifuge tubes and centrifuged for 10 min (3500 rpm). The plasma was separated, collected and stored under −80° C.

PK Data Under RLD Regimen

Plasma concentrations of the samples collected from Group I and Group IV animals are shown in Table 6.

Figure 7A:
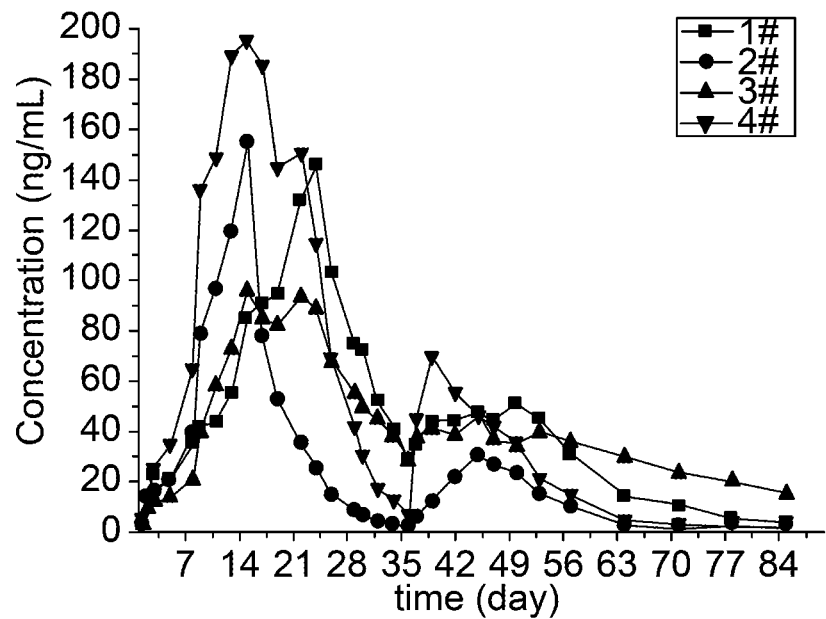
FIGS. 7A-7D show the PK curves of plasma concentration data obtained from animal studies under RLD Regimen.
Figure 7B:
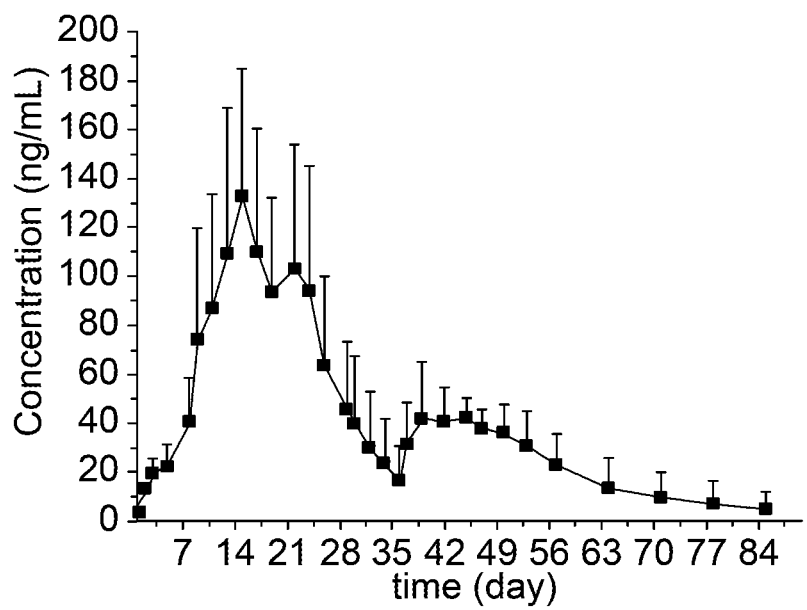

The PK data shown in Table 6 are plotted into various PK curves. FIG. 7A shows the PK curves of plasma concentration data obtained from Group I animals. FIG. 7B shows the PK curve based on the average plasma concentration data obtained from Group I animals.

Figure 7C:
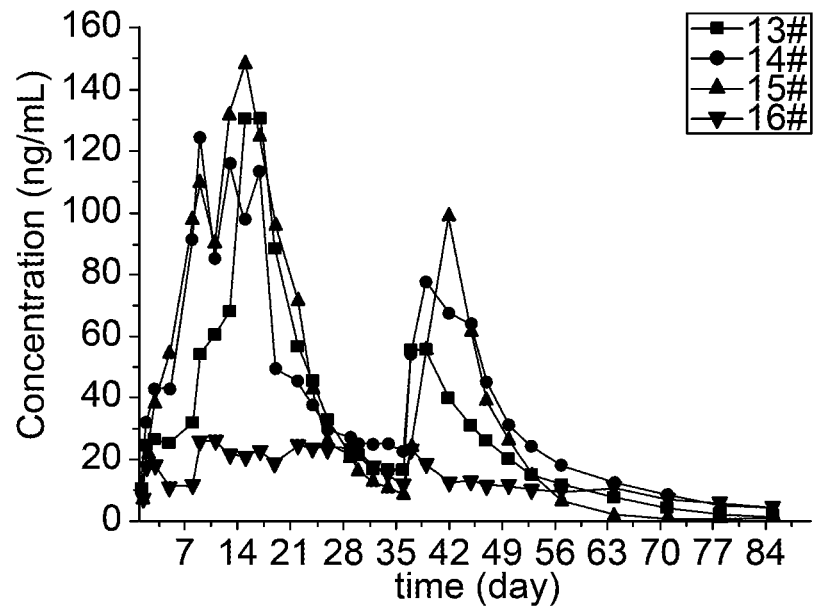
Figure 7D:
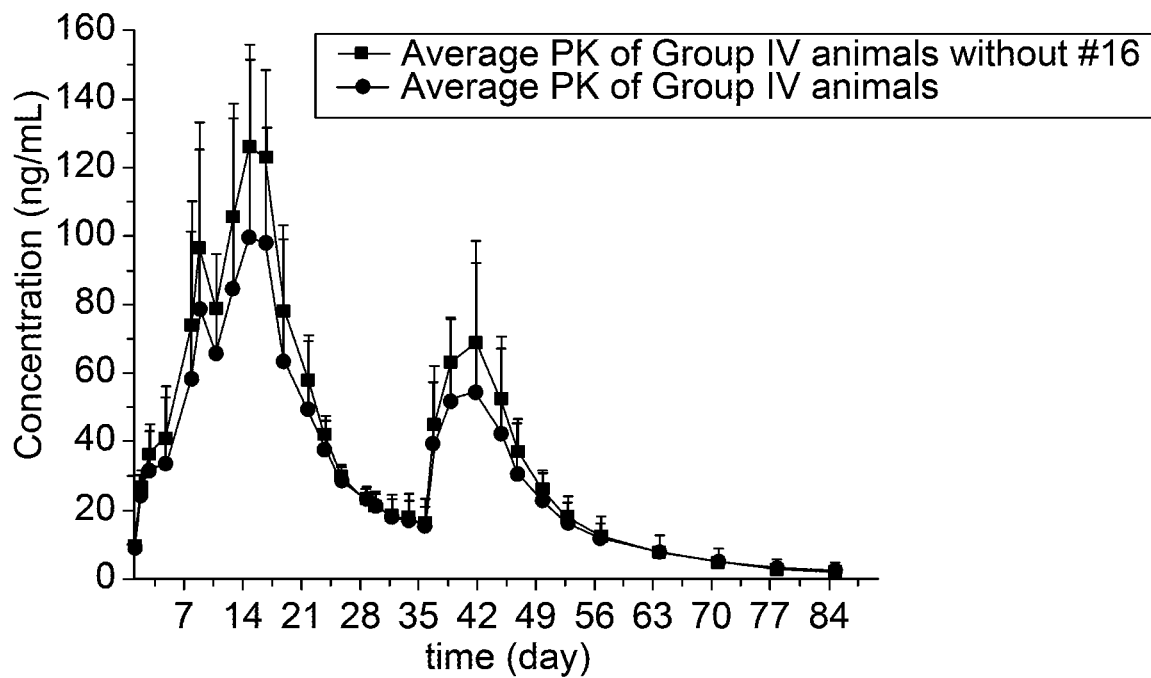

FIG. 7C shows the PK curves based on the plasma concentration data obtained from Group IV animals. Data from one animal (#16) appeared to deviate from its cohorts. FIG. 7D shows the respective PK curves based on the average data of Group IV animals with or without taking into consideration of data from #16 animal.

Table 7 summarizes the PK parameters derived from the PK curves for Groups I and IV animals. Standard deviation (SD) and coefficient of variation (CV %) are also provided.

TABLE 6

| Time | Plasma Concentration (ng/ml) | | | | | | Plasma Concentration (ng/ml) | | | | | |
|---|---|---|---|---|---|---|---|---|---|---|---|---|
| (day) | #1 | #2 | #3 | #4 | mean | SD | #13 | #14 | #15 | #16 | mean | SD |
| 1 | 0 | 0 | 0 | 0 | 0.00 | 0.00 | 0 | 0 | 0 | 0 | 0.00 | 0.00 |
| 1.25 | 2.87 | 5.52 | 2.79 | 2.43 | 3.40 | 1.42 | 10.7 | 9.29 | 7.59 | 7.22 | 8.70 | 1.61 |
| 2 | 14.2 | 15.6 | 9.97 | 12.6 | 13.09 | 2.42 | 24.8 | 32.1 | 22.3 | 17.7 | 24.23 | 6.02 |
| 3 | 23.1 | 16.7 | 13.1 | 25.6 | 19.63 | 5.74 | 26.7 | 43.1 | 38.3 | 18 | 31.53 | 11.34 |
| 5 | 20.4 | 20.1 | 14.4 | 34.7 | 22.40 | 8.65 | 25.3 | 42.8 | 54.9 | 11.1 | 33.53 | 19.27 |
| 8 | 35.7 | 40.1 | 21.1 | 65 | 40.48 | 18.26 | 31.95 | 91.5 | 98 | 11.7 | 58.29 | 42.99 |
| 9 | 42.5 | 79 | 39.9 | 136.5 | 74.48 | 45.04 | 54 | 124.5 | 110 | 25.8 | 78.58 | 46.50 |
| 11 | 43.7 | 96.9 | 58.4 | 148.5 | 86.88 | 46.81 | 60.5 | 85 | 90.5 | 26.5 | 65.63 | 29.16 |
| 13 | 55.5 | 119.5 | 73 | 189 | 109.25 | 59.63 | 68 | 116 | 132 | 21.75 | 84.44 | 49.86 |
| 15 | 85 | 155 | 96 | 195.5 | 132.88 | 51.84 | 130.5 | 98 | 148.5 | 20.6 | 99.40 | 56.54 |
| 17 | 91 | 78 | 85 | 185 | 109.75 | 50.45 | 130.5 | 113.5 | 125 | 22.9 | 97.98 | 50.55 |
| 19 | 94.5 | 53 | 82.5 | 144.5 | 93.63 | 38.14 | 88.5 | 49.45 | 96 | 18.95 | 63.23 | 35.88 |
| 22 | 132 | 35.75 | 93.5 | 150.5 | 102.94 | 50.70 | 56.5 | 45.5 | 71.6 | 24.5 | 49.53 | 19.82 |
| 24 | 146 | 25.65 | 89 | 115 | 93.91 | 51.13 | 45.5 | 38 | 43.1 | 23.5 | 37.53 | 9.86 |
| 26 | 103 | 15.15 | 67.5 | 68.5 | 63.54 | 36.24 | 33 | 29.7 | 26.3 | 23.5 | 28.13 | 4.12 |
| 29 | 74.8 | 9.14 | 55.7 | 42.1 | 45.44 | 27.67 | 21.8 | 27.1 | 20.8 | 23.9 | 23.40 | 2.78 |
| 30 | 72 | 7.17 | 50 | 30.5 | 39.92 | 27.64 | 21.5 | 25.1 | 16.3 | 22.6 | 21.38 | 3.70 |
| 32 | 52.6 | 4.52 | 45.5 | 17.6 | 30.06 | 22.76 | 16.7 | 24.9 | 13 | 18 | 18.15 | 4.97 |
| 34 | 40.5 | 3.1 | 37.7 | 13.1 | 23.60 | 18.39 | 17 | 25 | 11 | 14.9 | 16.98 | 5.90 |
| 36 | 28.9 | 2.46 | 28.4 | 7.15 | 16.73 | 13.90 | 16.8 | 22.6 | 8.65 | 11.7 | 14.94 | 6.12 |
| 37 | 35.4 | 6.59 | 38.2 | 45.2 | 31.35 | 17.01 | 55.5 | 54.3 | 24.2 | 23.1 | 39.28 | 18.05 |
| 39 | 44 | 12.8 | 41.3 | 69.4 | 41.88 | 23.15 | 55.5 | 77.6 | 55.8 | 18.8 | 51.93 | 24.39 |
| 42 | 44.6 | 22.5 | 39.1 | 55.7 | 40.48 | 13.83 | 39.9 | 67.6 | 99 | 12.7 | 54.80 | 37.02 |
| 45 | 47.7 | 30.8 | 45.2 | 45.9 | 42.40 | 7.80 | 31.1 | 64 | 61.7 | 12.9 | 42.43 | 24.75 |
| 47 | 44.7 | 27.1 | 37 | 42 | 37.70 | 7.75 | 26.2 | 45 | 39.6 | 11.3 | 30.53 | 15.06 |
| 50 | 51.2 | 23.6 | 34.5 | 35.5 | 36.20 | 11.36 | 20.3 | 31.1 | 26.5 | 11.7 | 22.40 | 8.39 |
| 53 | 45.2 | 15.6 | 40.2 | 21.3 | 30.58 | 14.34 | 15 | 24.4 | 15 | 10.3 | 16.18 | 5.91 |
| 57 | 30.9 | 10.3 | 36 | 14.9 | 23.03 | 12.36 | 11.9 | 18.1 | 6.95 | 9.96 | 11.73 | 4.71 |
| 64 | 14.9 | 3.41 | 30.3 | 4.78 | 13.35 | 12.41 | 7.9 | 12.6 | 2.1 | 10.5 | 8.28 | 4.54 |
| 71 | 10.8 | 0.5 | 23.8 | 3.3 | 9.60 | 10.42 | 4.35 | 8.72 | 1.08 | 7.42 | 5.39 | 3.41 |
| 78 | 5.88 | 0 | 20.6 | 1.72 | 7.05 | 9.36 | 2.23 | 5.21 | 0.5 | 6.24 | 3.55 | 2.65 |
| 85 | 3.86 | 0 | 15.5 | 0.5 | 4.97 | 7.23 | 1.38 | 4.11 | 0 | 4.6 | 2.52 | 2.20 |

TABLE 7

|  |  | $T_{max}$ d | $C_{max}$ µg/L | $AUC_{(0-t)}$ µg/L*d | $AUC_{(0-\infty)}$ µg/L*d | $T_{max-1}$ d | $C_{max-1}$ µg/L | $T_{max-2}$ d | $C_{max-2}$ µg/L |
|---|---|---|---|---|---|---|---|---|---|
| Group I | #1 | 24.00 | 146.00 | 3632.18 | 3682.95 | 24.00 | 146.00 | 50.00 | 51.20 |
| | #2 | 15.00 | 155.00 | 2010.03 | 2012.83 | 15.00 | 155.00 | 45.00 | 30.80 |
| | #3 | 15.00 | 96.00 | 3477.47 | 4010.14 | 15.00 | 96.00 | 45.00 | 45.20 |
| | #4 | 15.00 | 195.50 | 4210.47 | 4214.96 | 15.00 | 195.50 | 39.00 | 69.40 |
| | Mean | 17.25 | 148.13 | 3332.54 | 3480.22 | 17.25 | 148.13 | 44.75 | 49.15 |
| | SD | 4.50 | 40.88 | 936.41 | 1002.49 | 4.50 | 40.88 | 4.50 | 15.99 |
| | CV % | 26.09 | 27.60 | 28.10 | 28.81 | 26.09 | 27.60 | 10.06 | 32.52 |
| Group IV | #13 | 15.00 | 130.50 | 2528.69 | 2546.38 | 15.00 | 130.50 | 37.00 | 55.50 |
| | #14 | 9.00 | 124.50 | 3241.40 | 3312.15 | 9.00 | 124.50 | 39.00 | 77.60 |
| | #15 | 15.00 | 148.50 | 3191.02 | 3194.15 | 15.00 | 148.50 | 42.00 | 99.00 |
| | #16 | 11.00 | 26.50 | 1190.27 | 1311.82 | 11.00 | 26.50 | — | — |
| | Mean | 12.50 | 107.50 | 2537.85 | 2591.12 | 12.50 | 107.50 | 39.33 | 77.37 |
| | SD | 3.00 | 54.95 | 955.28 | 916.90 | 3.00 | 54.95 | 2.52 | 21.75 |
| | CV % | 24.00 | 51.12 | 37.64 | 35.39 | 24.00 | 51.12 | 6.40 | 28.11 |

PK Data Under Regimen A

Plasma concentrations of the samples collected from Group II animals are shown in Table 8.

TABLE 8

| Time | Concentration (ng/ml) | | | | | |
|---|---|---|---|---|---|---|
| (day) | #5 | #6 | #7 | #8 | mean | SD |
| 1 | 0 | 0 | 0 | 0 | 0.00 | 0.00 |
| 1.25 | 6.39 | 5.57 | 2.28 | 5.37 | 4.90 | 1.80 |
| 2 | 27.5 | 15.4 | 14.6 | 21.2 | 19.68 | 5.99 |
| 3 | 44.8 | 20.7 | 21.8 | 28.6 | 28.98 | 11.11 |
| 5 | 55.5 | 30.6 | 22.9 | 35.2 | 36.05 | 13.92 |
| 8 | 75.6 | 70.6 | 72.2 | 50 | 67.10 | 11.59 |
| 9 | 92.5 | 92.5 | 83.5 | 60 | 82.13 | 15.35 |
| 11 | 92.5 | 89 | 88.5 | 54 | 81.00 | 18.09 |
| 13 | 72 | 75 | 89 | 47.65 | 70.91 | 17.19 |
| 15 | 56.5 | 54 | 79.5 | 40.75 | 57.69 | 16.10 |
| 17 | 81.5 | 60.5 | 100 | 29.1 | 67.78 | 30.42 |
| 19 | 104 | 40.1 | 68.5 | 27.15 | 59.94 | 34.08 |
| 22 | 125 | 40.05 | 73.5 | 31.75 | 67.58 | 42.32 |
| 24 | 116.5 | 31.65 | 65 | 27.5 | 60.16 | 41.14 |
| 26 | 102 | 23.25 | 43.15 | 24.25 | 48.16 | 37.04 |
| 29 | 95.7 | 29.4 | 41.8 | 23.6 | 47.63 | 32.94 |
| 30 | 93.5 | 30.3 | 44.4 | 20.3 | 47.13 | 32.46 |
| 32 | 72 | 25.4 | 42.2 | 17.5 | 39.28 | 24.13 |
| 34 | 54.5 | 24 | 39.4 | 17.4 | 33.83 | 16.58 |

TABLE 8-continued

| Time | Concentration (ng/ml) | | | | | |
|---|---|---|---|---|---|---|
| (day) | #5 | #6 | #7 | #8 | mean | SD |
| 36 | 49.9 | 24.6 | 37.8 | 17.4 | 32.43 | 14.39 |
| 37 | 119.5 | 45.3 | 63.6 | 27.1 | 63.88 | 39.97 |
| 39 | 83.8 | 99.7 | 76.3 | 37.6 | 74.35 | 26.37 |
| 42 | 59.4 | 166 | 68.8 | 58.7 | 88.23 | 52.05 |
| 45 | 45.8 | 71.9 | 55 | 64.4 | 59.28 | 11.34 |
| 47 | 32.6 | 49.8 | 43.9 | 46.6 | 43.23 | 7.48 |
| 50 | 25.5 | 31.5 | 33.2 | 29 | 29.80 | 3.35 |
| 53 | 19.6 | 21.5 | 27.6 | 23.6 | 23.08 | 3.43 |
| 57 | 16.3 | 16.6 | 22.6 | 19.6 | 18.78 | 2.95 |
| 64 | 11.9 | 12.1 | 13.8 | 14.4 | 13.05 | 1.24 |
| 71 | 9.25 | 10.1 | 9.1 | 13.1 | 10.39 | 1.86 |
| 78 | 7.14 | 8.63 | 6.89 | 10 | 8.17 | 1.44 |
| 85 | 7.21 | 7.98 | 4.89 | 9.48 | 7.39 | 1.91 |

Figure 8A:
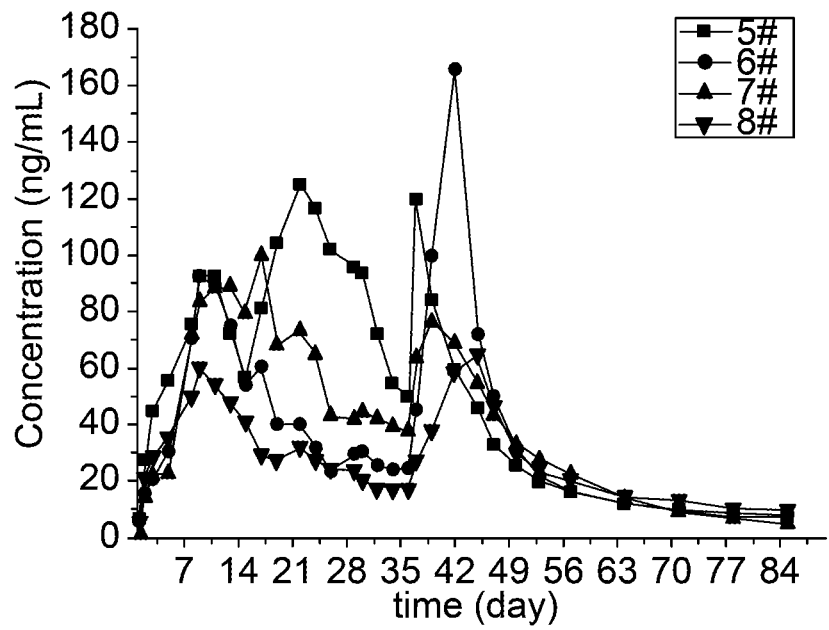
FIGS. 8A-8B shows the PK curves of plasma concentration data obtained from animal studies under a dosing regimen according to an embodiment.
Figure 8B:
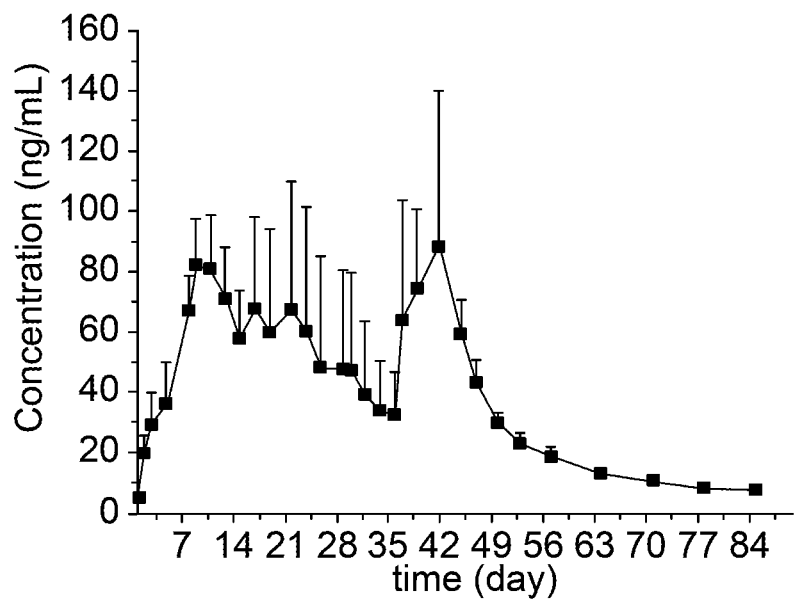

The PK data shown in Table 8 are plotted into various PK curves. FIG. 8A shows the PK curves of plasma concentration data obtained from Group II animals. FIG. 8B shows the PK curve based on the average plasma concentration data obtained from Group II animals.

Table 9 summarizes the PK parameters derived from the PK curves for Group II animals. Standard deviation (SD) and coefficient of variation (CV %) are also provided.

TABLE 9

|  | $T_{max}$ d | $C_{max}$ µg/L | $AUC_{(0-t)}$ µg/L*d | $AUC_{(0-\infty)}$ µg/L*d | $T_{max-1}$ d | $C_{max-1}$ µg/L | $T_{max-2}$ d | $C_{max-2}$ µg/L |
|---|---|---|---|---|---|---|---|---|
| #5 | 22.00 | 125.00 | 4069.12 | 4285.47 | 22.00 | 125.00 | 37.00 | 119.50 |
| #6 | 42.00 | 166.00 | 3146.75 | 3544.02 | 9.00 | 92.50 | 42.00 | 166.00 |
| #7 | 17.00 | 100.00 | 3336.44 | 3446.66 | 17.00 | 100.00 | 39.00 | 76.30 |
| #8 | 45.00 | 64.40 | 2282.89 | 2612.80 | 9.00 | 60.00 | 45.00 | 64.40 |
| Mean | 31.50 | 113.85 | 3208.80 | 3472.24 | 14.25 | 94.38 | 40.75 | 106.55 |
| SD | 14.06 | 42.74 | 734.30 | 684.54 | 6.40 | 26.80 | 3.50 | 46.17 |
| CV % | 44.63 | 37.54 | 22.88 | 19.71 | 44.89 | 28.40 | 8.59 | 43.33 |

PK Data Under Regimen B

Plasma concentrations of the samples collected from Group III and Group V animals are shown in Table 10.

Figure 9A:
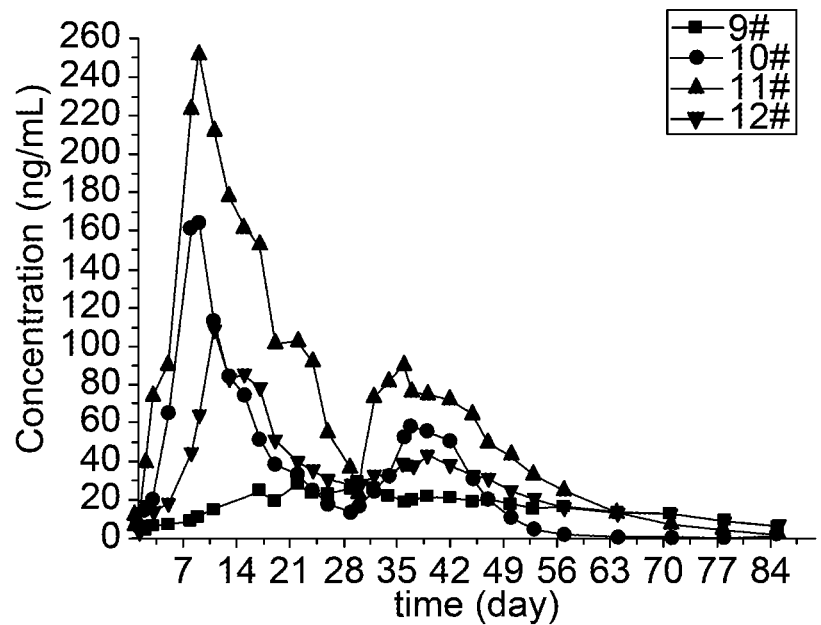
FIG. 9A-9D show the PK curves of plasma concentration data obtained from animal studies under a dosing regimen according to another embodiment.
Figure 9B:
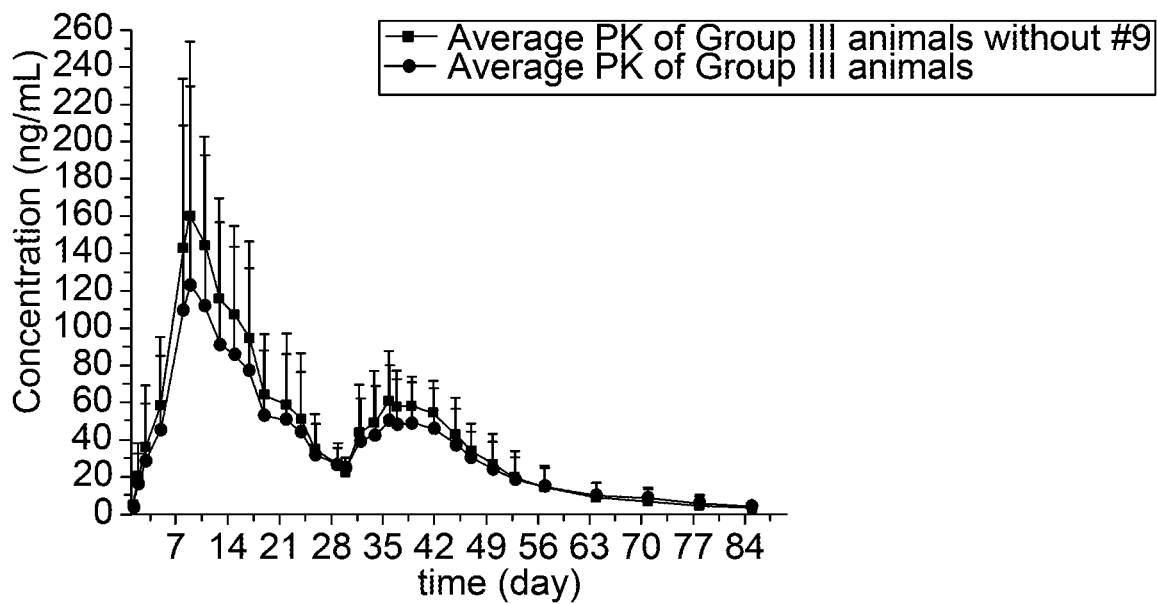

The PK data shown in Table 10 are plotted into various PK curves. FIG. 9A shows the PK curves of Group III animal data. Data from one animal (#9) appeared to deviate from its cohorts. FIG. 9B shows the respective PK curves based on the average data of Group III animals (with or without taking into consideration of data from #9 animal).

Figure 9C:
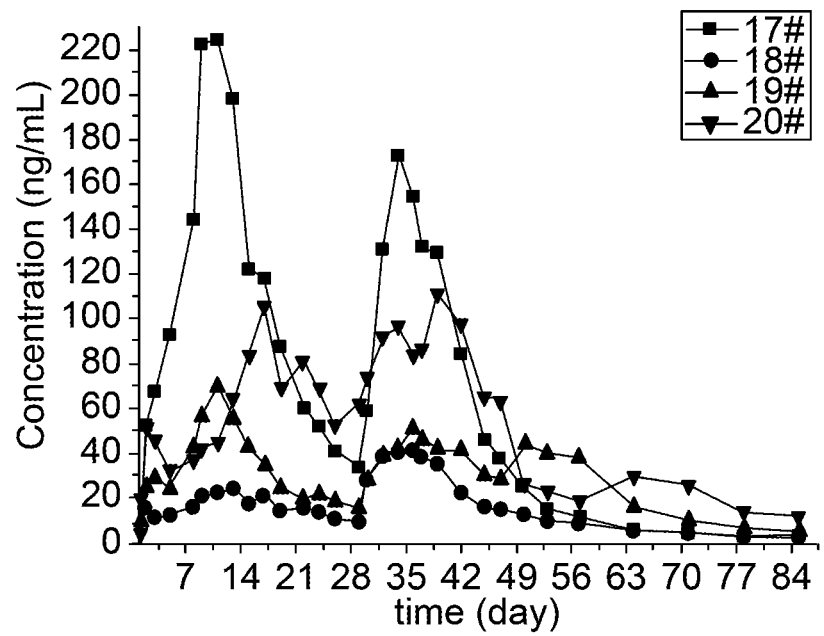
Figure 9D:
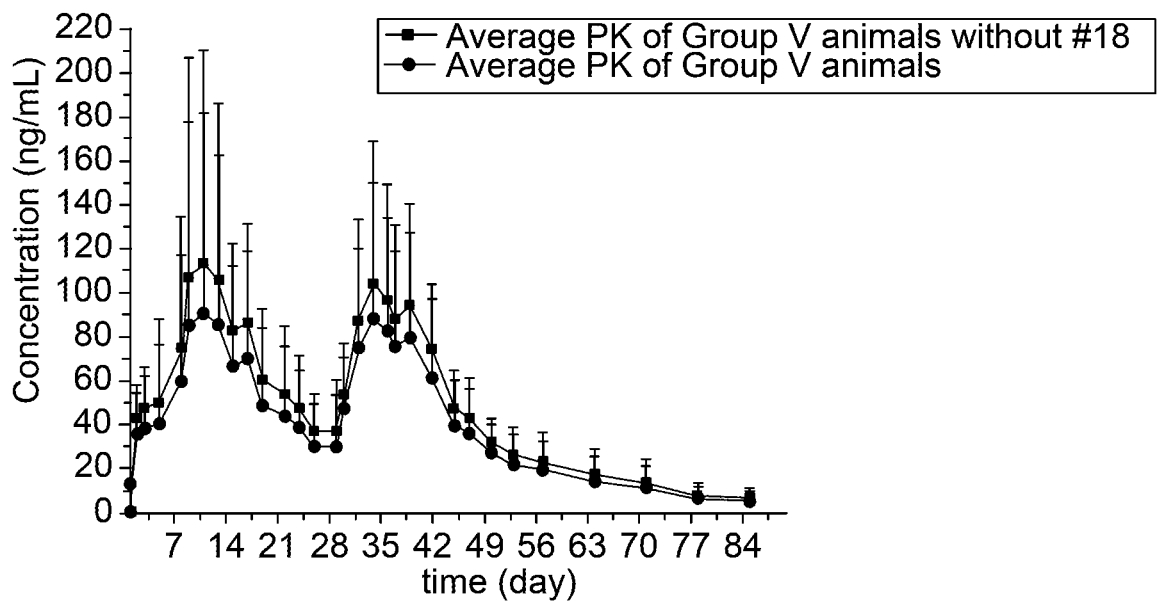

FIG. 9C shows the PK curves of Group V animal data. Data from one animal (#18) appeared to deviate from its cohorts. FIG. 9D shows the respective PK curves based on the average data of Group V animals (with or without taking into consideration of data from #18 animal).

TABLE 10

| Time | Plasma Concentration (ng/ml) | | | | | | Plasma Concentration (ng/ml) | | | | | |
|---|---|---|---|---|---|---|---|---|---|---|---|---|
| (day) | #9 | #10 | #11 | #12 | mean | SD | #17 | #18 | #19 | #20 | mean | SD |
| 1 | 0 | 0 | 0 | 0 | 0.00 | 0.00 | 0 | 0 | 0 | 0 | 0.00 | 0.00 |
| 1.25 | 2.36 | 3.61 | 7.12 | 1.34 | 3.61 | 2.52 | 15.8 | 6.85 | 9.08 | 19.5 | 12.81 | 5.86 |
| 2 | 4.26 | 14.1 | 40.2 | 7.03 | 16.40 | 16.40 | 52.1 | 15.3 | 24.8 | 51.2 | 35.85 | 18.66 |
| 3 | 6.35 | 19.9 | 74.1 | 13.8 | 28.54 | 30.88 | 67.1 | 11.6 | 29 | 45.9 | 38.40 | 23.71 |
| 5 | 7.19 | 65.2 | 90.7 | 18 | 45.27 | 39.39 | 9. | 12.8 | 24.6 | 32.3 | 40.68 | 35.79 |
| 8 | 9.3 | 161.5 | 223 | 44.3 | 109.53 | 99.80 | 144 | 16.35 | 42.25 | 37.05 | 59.91 | 57.16 |
| 9 | 11.05 | 164.5 | 252 | 64 | 122.89 | 107.05 | 222.5 | 21.45 | 55.5 | 42 | 85.36 | 92.49 |
| 11 | 14.95 | 112.5 | 212 | 108 | 111.86 | 80.49 | 224.5 | 22.7 | 70 | 44.65 | 90.46 | 91.42 |
| 13 | 18.35 | 84.5 | 178 | 83 | 90.96 | 65.71 | 198.5 | 24 | 55.5 | 64 | 85.50 | 77.27 |
| 15 | 21.15 | 75 | 161.5 | 85.5 | 85.79 | 57.81 | 122 | 17.65 | 42.55 | 83.5 | 66.43 | 45.93 |
| 17 | 24.65 | 52 | 152.5 | 78.5 | 76.91 | 54.98 | 118 | 21.2 | 35 | 105.5 | 69.93 | 48.89 |
| 19 | 19.7 | 38.7 | 101.5 | 51 | 52.73 | 34.97 | 87.5 | 14.15 | 24.55 | 69 | 48.80 | 35.09 |
| 22 | 28.4 | 33.4 | 102.5 | 39.55 | 50.96 | 34.66 | 60 | 15.7 | 19.9 | 80.9 | 44.13 | 31.62 |
| 24 | 24 | 25.1 | 91.5 | 35.25 | 43.96 | 32.09 | 51.8 | 13.6 | 21.5 | 68.8 | 38.93 | 25.84 |
| 26 | 23.2 | 17.8 | 55.5 | 30.35 | 31.71 | 16.67 | 40.4 | 10.7 | 18.2 | 51.8 | 30.28 | 19.10 |
| 29 | 26.1 | 14 | 36.4 | 28.1 | 26.15 | 9.25 | 33.7 | 9.8 | 15.3 | 61.5 | 30.08 | 23.31 |
| 30 | 29.7 | 17.1 | 23.1 | 27.9 | 24.45 | 5.64 | 59.2 | 27.9 | 28 | 73.6 | 47.18 | 22.96 |
| 32 | 26.2 | 24.9 | 73 | 32.4 | 39.13 | 22.82 | 131 | 38.5 | 38.9 | 91.9 | 75.08 | 44.93 |
| 34 | 22.4 | 32.9 | 81.4 | 32.6 | 42.33 | 26.50 | 172.5 | 40.6 | 42.6 | 96.5 | 88.05 | 61.97 |
| 36 | 18.9 | 52.7 | 89.9 | 38.7 | 50.05 | 29.97 | 154.5 | 41.1 | 50.7 | 84 | 82.58 | 51.35 |
| 37 | 19.9 | 58.3 | 76 | 37.6 | 47.95 | 24.41 | 131.5 | 38.2 | 46 | 86.3 | 75.50 | 42.87 |
| 39 | 21.9 | 55.7 | 74.7 | 42.9 | 48.80 | 22.19 | 129.5 | 35.2 | 41.6 | 111 | 79.33 | 47.93 |
| 42 | 21 | 51.1 | 72.3 | 38.1 | 45.63 | 21.64 | 84.3 | 22.2 | 41.1 | 97.6 | 61.30 | 35.51 |
| 45 | 19.2 | 30.9 | 64.7 | 32.4 | 36.80 | 19.51 | 45.8 | 16.5 | 30.2 | 65.2 | 39.43 | 20.94 |
| 47 | 20.7 | 20.5 | 49.5 | 31 | 30.43 | 13.63 | 37.8 | 14.9 | 28 | 63.3 | 36.00 | 20.48 |
| 50 | 17.7 | 10.9 | 43.6 | 24.4 | 24.15 | 14.09 | 25.1 | 12.3 | 44.1 | 26.6 | 27.03 | 13.07 |
| 53 | 15.6 | 4.92 | 32.9 | 20.3 | 18.43 | 11.60 | 15.1 | 9.8 | 40 | 23.1 | 22.00 | 13.19 |
| 57 | 16.8 | 2.23 | 24.8 | 16.2 | 15.01 | 9.38 | 12 | 8.69 | 38.2 | 18.6 | 19.37 | 13.21 |
| 64 | 13.6 | 0.5 | 13.4 | 12.9 | 10.10 | 6.41 | 5.67 | 5.24 | 16 | 29.6 | 14.13 | 11.45 |
| 71 | 12.8 | 0 | 7.62 | 12.7 | 8.28 | 6.03 | 3.59 | 4.32 | 10.2 | 25.6 | 10.93 | 10.22 |
| 78 | 9.27 | 0 | 4.46 | 9.05 | 5.70 | 4.40 | 2.6 | 2.71 | 6.54 | 13.8 | 6.41 | 5.25 |
| 85 | 6.3 | 0 | 2.7 | 6.71 | 3.93 | 3.18 | 2.28 | 2.17 | 5.2 | 11.4 | 5.26 | 4.33 |

Table 11 summarizes the PK parameters derived from the PK curves for Groups III and V animals. Standard deviation (SD) and coefficient of variation (CV %) are also provided.

TABLE 11

| | | $T_{max}$ d | $C_{max}$ µg/L | $AUC_{(0-t)}$ µg/L*d | $AUC_{(0-\infty)}$ µg/L*d | $T_{max-1}$ d | $C_{max-1}$ µg/L | $T_{max-2}$ d | $C_{max-2}$ µg/L |
|---|---|---|---|---|---|---|---|---|---|
| Group III | #9 | 30.00 | 29.70 | 1393.52 | 1517.94 | 22.00 | 28.40 | 30.00 | 29.70 |
| | #10 | 9.00 | 164.50 | 2522.18 | 2522.83 | 9.00 | 164.50 | 37.00 | 58.30 |
| | #11 | 9.00 | 252.00 | 5364.80 | 5401.23 | 9.00 | 252.00 | 36.00 | 89.90 |
| | #12 | 11.00 | 108.00 | 2561.81 | 2709.05 | 11.00 | 108.00 | 39.00 | 42.90 |
| | Mean | 14.75 | 138.55 | 2960.58 | 3037.76 | 12.75 | 138.23 | 35.50 | 55.20 |
| | SD | 10.21 | 93.68 | 1691.86 | 1660.22 | 6.24 | 94.18 | 3.87 | 25.92 |
| | CV % | 69.22 | 67.61 | 57.15 | 54.65 | 48.93 | 68.14 | 10.91 | 46.95 |
| Group V | #17 | 11.00 | 224.50 | 5170.74 | 5195.24 | 11.00 | 224.50 | 34.00 | 172.50 |
| | #18 | 36.00 | 41.10 | 1214.94 | 1256.99 | 13.00 | 24.00 | 36.00 | 41.10 |
| | #19 | 11.00 | 70.00 | 2387.95 | 2483.33 | 11.00 | 70.00 | 36.00 | 50.70 |
| | #20 | 39.00 | 111.00 | 4121.45 | 4350.73 | 17.00 | 105.50 | 39.00 | 111.00 |
| | Mean | 24.25 | 111.65 | 3223.77 | 3321.57 | 13.00 | 106.00 | 36.25 | 93.83 |
| | SD | 15.35 | 80.51 | 1763.57 | 1782.79 | 2.83 | 85.76 | 2.06 | 60.89 |
| | CV % | 63.29 | 72.11 | 54.71 | 53.67 | 21.76 | 80.90 | 5.69 | 64.90 |

Discussions

Based on the animal studies and the in vivo PK data obtained, the following observations are made with regard to the dosing regimens of the paliperidone palmitate injectable suspension according to the embodiments disclosed herein.

Figure 10A:
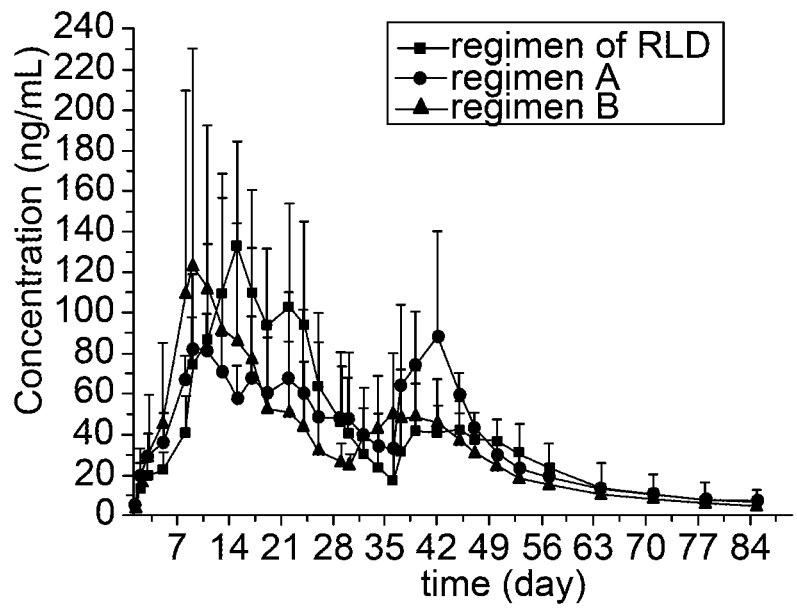
FIG. 10A shows the average PK curves based on plasma concentration data obtained from animal studies in different dosing regimens.

FIG. 10A shows the average PK curves based on the plasma concentration data obtained from animals of Groups I (standard RLD Regimen), Group II (Regimen A) and Group III (Regimen B). As shown, with the heightened initial dose of 225 mg human equivalent dose of paliperidone as paliperidone palmitate, Regimen B reached $C_{max}$ earlier ($T_{max}\approx14$ days) than RLD Regimen ($T_{max}\approx17$ days) did, even though the latter had a combined first and second loading of 250 mg (human equivalent dose). Under Regimen B, the $C_{max}$ was comparable to that of RLD Regimen despite having a heightened loading dose, thus alleviating concerns of adverse effects associated with the plasma concentrations of paliperidone being too high. Furthermore, despite the longer interval between the first and second dose under Regimen B, the trough (day 28) was comparable to the plasma concentration on day 28 under RLD Regimen and was indeed higher than the trough under the RLD Regimen (day 35). The overall drug exposures (AUC) are comparable for all three Regimens.

Figure 10B:
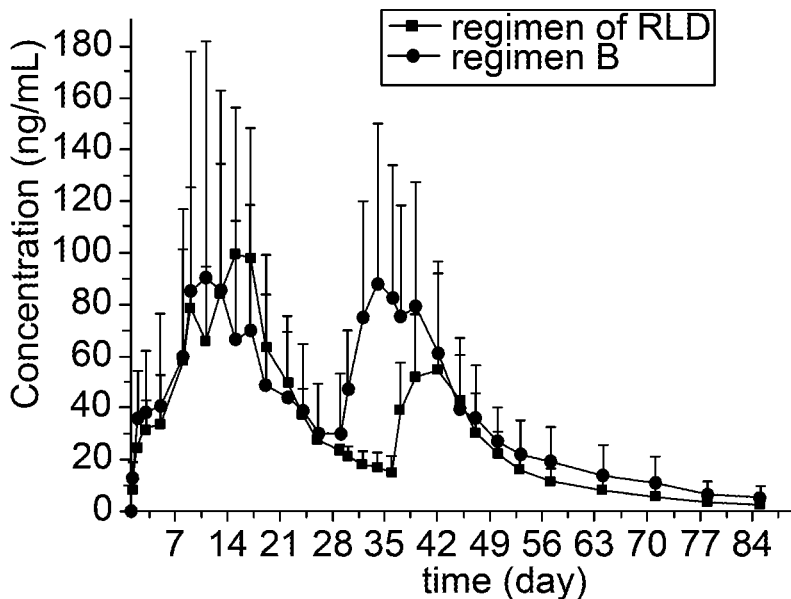
FIG. 10B shows the average PK curves based on plasma concentration data obtained from studies in different dosing regimens.

FIG. 10B shows the average PK curves based on plasma concentration data obtained from animals of Groups IV (RLD Regimen) and Group V (Regimen B). Consistent with the results shown in FIG. 10A, Regimen B reached $C_{max}$ earlier, despite having only a single loading dose that is lower than the combined first and second loading doses of RLD Regimen. Under Regimen B, despite having a heightened initial loading dose, the $C_{max}$ was comparable to that of RLD Regimen. In addition, under Regimen B, the trough (day 28) was comparable to the same-day concentration of RLD Regimen and higher than the trough of the RLD Regimen.

The in vivo data based on the animal studies appear consistent with the simulated data shown in Example 3 (see Table 4).

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including but not limited to U.S. Provisional Patent Application No. 62/578,082, filed Oct. 27, 2017, and U.S. Provisional Patent Application No. 62/647,333, filed Mar. 23, 2018, are incorporated herein by reference in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A dosing regimen for administering paliperidone palmitate to a patient in need of treatment of schizophrenia or schizoaffective disorders, the dosing regimen consisting of:
   (1) administering intramuscularly to the patient an initial dose of 312 mg-468 mg paliperidone palmitate on the first day of treatment; and
   (2) beginning on the 29th day±7 days from the initial dose, administering intramuscularly to the patient one or more monthly doses in the range of 39 mg to 234 mg paliperidone palmitate, wherein each dose of paliperidone palmitate is formulated in an aqueous suspension formulation.

2. The dosing regimen of claim 1 wherein the initial dose comprises 351 mg paliperidone palmitate.

3. The dosing regimen of claim 1 wherein each of the one or more monthly doses comprises 117 mg paliperidone palmitate.

4. The dosing regimen of claim 1 wherein the paliperidone palmitate is in the form of submicron-sized particles having specific surface areas in the range of 2-15 m²/g.

5. The dosing regimen of claim 1 as a monotherapy.

6. The dosing regimen of claim 1 as an adjunct therapy to antidepressant or mood stabilizer.

7. The dosing regimen of claim 1 wherein the aqueous suspension formulation for each dose comprises:
   (a) from 3 to 20% (w/w) of the paliperidone palmitate having a mass median diameter (d(0.5)) in the range of 900 nm-1.2 µm;
   (b) from 0.5 to 3% (w/w) of polysorbate 20;
   (c) from 0.5 to 4% (w/w) of polyethylene glycol 4000; and
   (d) up to 2% (w/w) preservatives; and
   (e) water q.s. ad 100%, wherein the formulation has a pH in the range of 7-8.5.

8. The dosing regimen of claim 7 wherein the aqueous suspension composition for each dose comprises, by w/w %,
   15.04% of paliperidone palmitate;
   0.48% of citric acid monohydrate;
   0.48% disodium hydrogen phosphate anhydrous;
   0.24% sodium dihydrogen phosphate monohydrate;
   0.27% sodium hydroxide;
   2.89% polyethylene glycol 4000;
   1.16% polysorbate 20; and
   79.43% water.

9. A dosing regimen for administering paliperidone palmitate to a patient in need of treatment of schizophrenia or schizoaffective disorders, the dosing regimen consisting of:
   (1) administering intramuscularly to the patient an initial dose of 312 mg-468 mg paliperidone palmitate on the first day of treatment; and
   (2) beginning on the 29th day±7 days from the initial dose, administering intramuscularly to the patient a regular monthly dosing regimen, wherein the regular monthly dosing regimen comprises one or more monthly doses in the range of 39 mg to 234 mg paliperidone palmitate, wherein each dose of paliperidone palmitate is formulated in an aqueous suspension formulation.

10. The dosing regimen of claim 9, wherein the initial dose comprises 351 mg paliperidone palmitate.

11. The dosing regimen of claim 9, wherein each of the one or more monthly doses comprises 117 mg paliperidone palmitate.

12. The dosing regimen of claim 9 wherein the paliperidone palmitate is in the form of submicron-sized particles having specific surface areas in the range of 2-15 m²/g.

13. The dosing regimen of claim 9 as a monotherapy.

14. The dosing regimen of claim 9 as an adjunct therapy to antidepressant or mood stabilizer.

15. The dosing regimen of claim 9 wherein the aqueous suspension formulation for each dose comprises:
   (a) from 3 to 20% (w/w) of the paliperidone palmitate having a mass median diameter (d(0.5)) in the range of 900 nm-1.2 µm;
   (b) from 0.5 to 3% (w/w) of polysorbate 20;
   (c) from 0.5 to 4% (w/w) of polyethylene glycol 4000; and
   (d) up to 2% (w/w) preservatives; and
   (e) water q.s. ad 100%, wherein the formulation has a pH in the range of 7-8.5.

16. The dosing regimen of claim 15 wherein the aqueous suspension composition for each dose comprises, by w/w %,
   15.04% of paliperidone palmitate;
   0.48% of citric acid monohydrate;
   0.48% disodium hydrogen phosphate anhydrous;
   0.24% sodium dihydrogen phosphate monohydrate;
   0.27% sodium hydroxide;
   2.89% polyethylene glycol 4000;
   1.16% polysorbate 20; and
   79.43% water.

17. A dosing regimen for administering paliperidone palmitate to a patient in need of treatment of schizophrenia or schizoaffective disorders, the dosing regimen comprising:
   (1) administering intramuscularly to the patient an initial dose of 351 mg paliperidone palmitate on the first day of treatment; and
   (2) beginning on the 29th day±7 days from the initial dose, administering intramuscularly to the patient one or more monthly doses in the range of 39 mg to 234 mg paliperidone palmitate, wherein each dose of paliperidone palmitate is formulated in an aqueous suspension formulation.

18. The dosing regimen of claim 17, wherein each of the one or more monthly doses comprises 117 mg paliperidone palmitate.

19. The dosing regimen of claim 17 wherein the paliperidone palmitate is in the form of submicron-sized particles having specific surface areas in the range of 2-15 $m^2/g$.

20. The dosing regimen of claim 17 as a monotherapy.

21. The dosing regimen of claim 17 as an adjunct therapy to antidepressant or mood stabilizer.

22. The dosing regimen of claim 17 wherein the aqueous suspension formulation for each dose comprises:
   (a) from 3 to 20% (w/w) of the paliperidone palmitate having a mass median diameter (d(0.5)) in the range of 900 nm-1.2 µm;
   (b) from 0.5 to 3% (w/w) of polysorbate 20;
   (c) from 0.5 to 4% (w/w) of polyethylene glycol 4000; and
   (d) up to 2% (w/w) preservatives; and
   (e) water q.s. ad 100%, wherein the formulation has a pH in the range of 7-8.5.

23. The dosing regimen of claim 22 wherein the aqueous suspension composition for each dose comprises, by w/w %,
   15.04% of paliperidone palmitate;
   0.48% of citric acid monohydrate;
   0.48% disodium hydrogen phosphate anhydrous;
   0.24% sodium dihydrogen phosphate monohydrate;
   0.27% sodium hydroxide;
   2.89% polyethylene glycol 4000;
   1.16% polysorbate 20; and
   79.43% water.

* * * * *